United States Patent [19]

Patel

[11] 3,995,629
[45] Dec. 7, 1976

[54] ANESTHESIA DEVICE
[75] Inventor: Bhupendra C. Patel, Elgin, Ill.
[73] Assignee: The Kendall Company, Boston, Mass.
[22] Filed: June 23, 1975
[21] Appl. No.: 589,508
[52] U.S. Cl. .............................. 128/215; 128/221
[51] Int. Cl.² ........................................ A61M 5/00
[58] Field of Search .......... 128/215, 221, 347, 348, 128/216, 260, 2 B, 214.4, 349, 218 R, 218 F

[56] References Cited
UNITED STATES PATENTS

| | | | |
|---|---|---|---|
| 2,700,385 | 1/1955 | Ortiz | 128/215 |
| 2,712,314 | 7/1955 | Kohl | 128/215 |
| 2,740,404 | 4/1956 | Kohl | 128/215 |
| 2,876,770 | 3/1959 | White | 128/215 |
| 2,880,724 | 4/1959 | Velarde | 128/215 |
| 3,380,448 | 4/1968 | Sadove et al. | 128/215 |
| 3,394,699 | 7/1968 | Koett | 128/2 B |
| 3,508,545 | 4/1970 | Reif et al. | 128/214.4 |
| 3,595,217 | 7/1971 | Rheinfrank | 128/215 |

FOREIGN PATENTS OR APPLICATIONS 257,747  4/1965  Australia ........................... 128/2 B Primary Examiner—John D. Yasko
Attorney, Agent, or Firm—Powell L. Sprunger

[57] ABSTRACT

A device for performing an anesthesia procedure on a patient comprising, sleeve means having an end portion for placement adjacent the patient's body, and hollow needle means received in the sleeve means for relative longitudinal movement thereof, with the needle means having a tip for penetrating the patient's body. The device has means for biasing the sleeve means and needle means relative each other for exposing the tip from the end portion and puncturing the patient's body.

30 Claims, 11 Drawing Figures

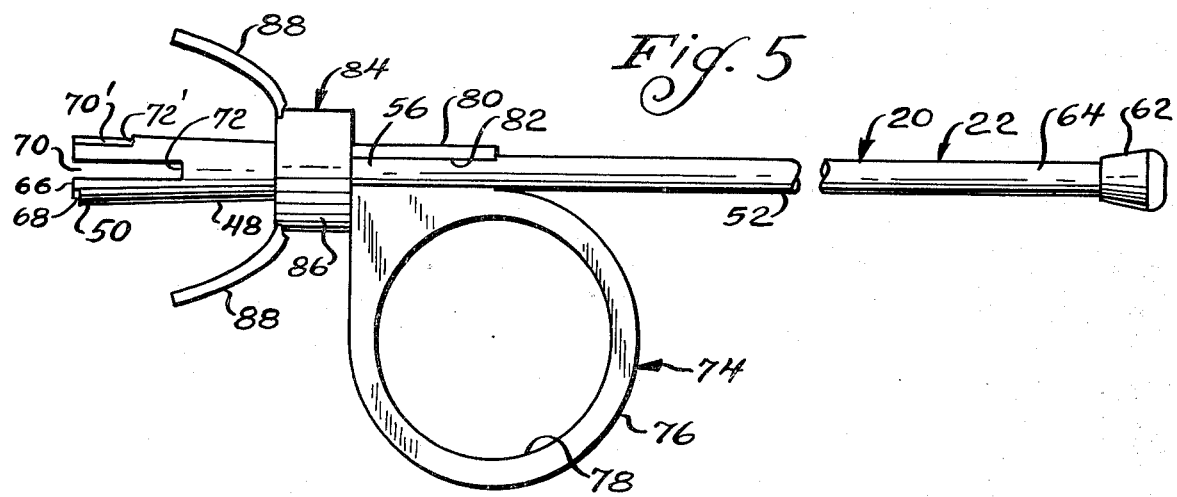
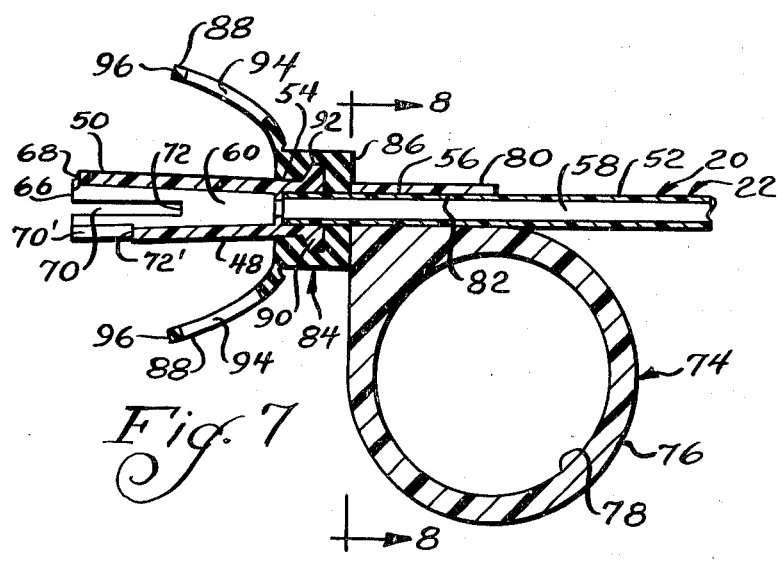
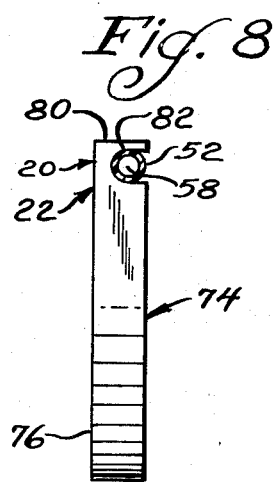
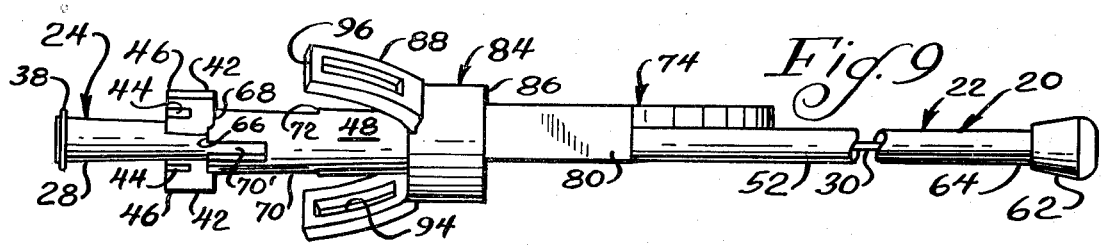
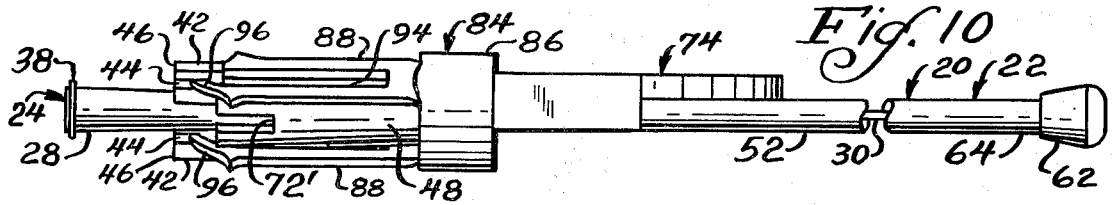
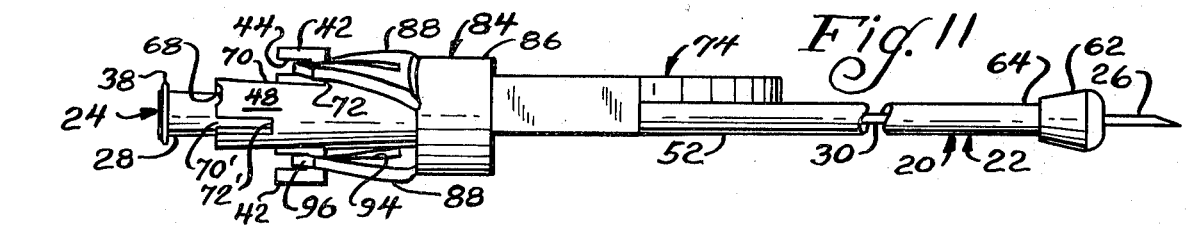

ANESTHESIA DEVICE

BACKGROUND OF THE INVENTION

The present invention relates to devices for performing an anesthesia procedure.

During childbirth, paracervical and trans-pudendal anesthesia procedures are commonly used to reduce pain during the first and second stages of labor. The first stage of labor may be defined as the period of time between the onset of labor and the time at which the cervix has completely dilated. The second stage of labor takes place between the time at which the cervix has completely dilated and the time of child delivery. Pain during the first stage of labor is primarily caused by effacement and dilation of the cervix, and may be relieved by a paracervical block. Pain during the second stage of labor results from dilation of the vagina, pressure exerted against the pelvic bones, and episiotomy, and may be relieved with a pudendal block.

The paracervical anesthesia procedure is normally performed when the cervix has dilated approximately 4 centimeters, with uterine contractions taking place at approximately 5 minute intervals and lasting at least 30 seconds. The paracervical block may be either a single injection or a continuous type, and is performed to block the nerves around the cervical opening.

During the procedure, the physician inserts a needle and catheter assembly into the vagina with the needle retracted within the assembly, and places the distal end of the assembly against the ligament at the vaginal fornix immediately lateral to its junction with the cervix. Next, the needle is pushed out of the assembly by the physician, and should penetrate the mucosa approximately 1.0 to 1.5 centimeters, after which the anesthetic solution is injected through the needle into the mucosa. In this manner, the anesthetic solution may be injected at 3 or 4 and 8 or 9 o'clock positions into the mucosa around the cervix to obtain the paracervical block.

When the cervix has almost fully dilated, the transpudendal anesthesia procedure is performed to relieve pain during the second stage of labor. in this procedure, the anesthetic solution is injected into the wall of the vagina.

During the paracervical anesthesia procedure, care must be taken to prevent over penetration of the needle or assembly in the mucosa, resulting in possible harm or death to the infant. When the physician pushes on a proximal end of the needle of present devices to penetrate the mucosa with the needle tip, the distal end of the assembly may become depressed into and stretch the mucosa. Consequently, the needle tip and possibly the distal portion of the assembly may pass through the mucosa. Also, the distal end of the assembly may slip while the physician applies force to the needle, causing the needle to penetrate the body at the wrong location. In certain of the present devices, the needle may slip from the assembly is being positioned, resulting in needle penetration before the assembly has been properly placed for performing the procedure.

SUMMARY OF THE INVENTION

The principal feature of the present invention is the provision of a device for performing an anesthesia procedure in a simplified and sure manner.

The device of the present invention comprises, elongated sleeve means having a proximal end, and a distal end for placement adjacent the patient's body. The device has elongated hollow needle means slidably received in the sleeve means and having a tip for penetrating the patient's body. The needle means is movable between a first position with the needle tip retracted within the sleeve means, and a second position with the needle tip extending from the distal end of the sleeve means for puncturing the patient's body. The device has means for urging the needle means between teh first and second positions.

A feature of the present invention is the provision of means for locking the needle means at its first position to prevent premature penetration of the needle tip into the patient's body.

Another feature of the present invention is that the locking means may be released in order that the urging means biases the needle means to a second position for penetrating into the patient's body in a controlled manner.

Thus, a feature of the invention is that body penetration of the needle tip is obtained without applying longitudinal force to the needle means by the physician.

A further feature of the present invention is that the device minimizes the possibility of slippage while the device is being positioned prior to needle penetration.

Still another feature of the invention is that the device minimizes the possibility that the distal end of the sleeve means will depress into the patient's body prior to needle penetration.

Thus, another feature of the present invention is that the device minimizes the possibility that the needle tip will overpenetrate into the patient's body.

A feature of the invention is that the physician may select the depth the needle penetrates into the patient's body.

A further feature of the invention is that the needle tip quickly penetrates into the patient's body to reduce trauma to the patient.

Still another feature of the invention is that the physician may control penetration of the needle tip into the patient's body, if desired.

Yet another feature of the invention is that the physician may disconnect the urging means from the device, if desired.

Further features will become more fully apparent in the following description of the embodiments of this invention and from the appended claims.

DESCRIPTION OF THE DRAWINGS

In the drawings:

FIG. 5 is a fragmentary elevational view of the sleeve means;

FIG. 7 is a fragmentary sectional view of a proximal end of the sleeve means and the driving member;

FIG. 8 is a sectional view taken substantially as indicated along the line 8—8 of FIG. 7;

FIG. 9 is a fragmentary top plan view of the device, showing the driving member disconnected from the needle means, and the needle means locked in a first position with the needle tip retracted within the sleeve means;

FIG. 10 is a fragmentary top plan view of the device, showing the driving member connected to the needle means, with the needle means locked in its firt position; and FIG. 11 is a fragmentary top plan view of the device, showing the needle means in a second position with the needle tip projecting out of the sleeve means to penetrate the patient's body.

DESCRIPTION OF THE PREFERRED EMBODIMENTS

Figure 1:
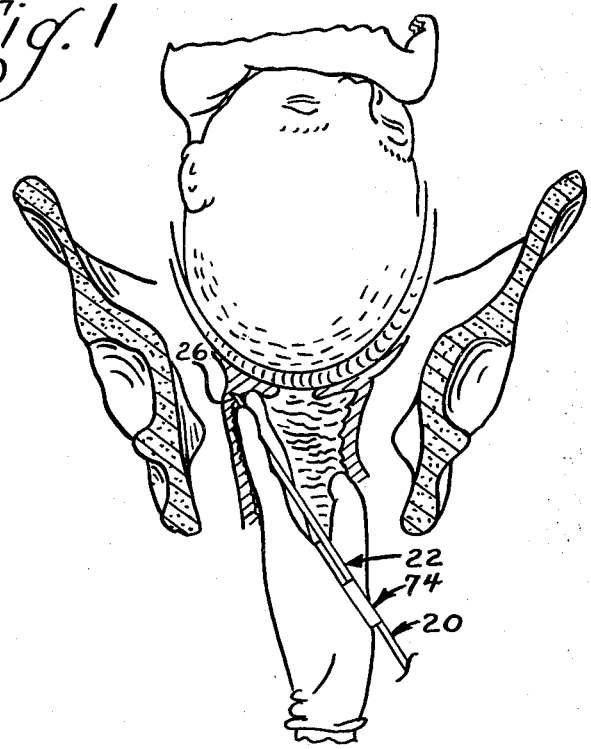
FIG. 1 is a fragmentary perspective view of the device of the present invention as positioned for performing a paracervical anesthesia procedure.
Figure 2:
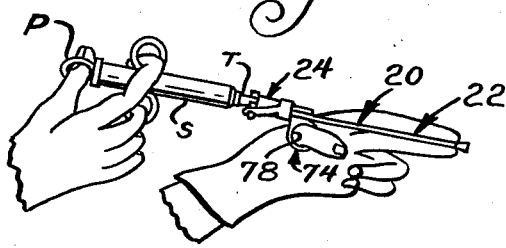
FIG. 2 is an elevational view of the device of FIG. 1, showing needle means of the device as retracted within sleeve means of the device.
Figure 3:
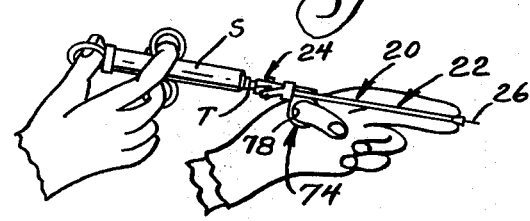
FIG. 3 is an elevational view of the device, showing a tip of the needle extending from the sleeve means for penetrating the patient's body.

Referring now to FIGS. 1–3, there is shown a device generally designated 20 for performing an anesthesia procedure, and, in particular, a paracervical or transpudendal anesthesia procedure. The device 20 has a sleeve assembly or sleeve means 22, and a hollow needle assembly or needle means 24 slidably received within the sleeve assembly 22. As shown in FIGS. 2 and 3, the needle assembly 24 may be moved between a first longitudinal position in the sleeve assembly 22 with a tip 26 of the needle assembly retracted within the sleeve assembly 22, and a second longitudinal position with the tip 26 of the needle assembly 24 extending from the sleeve assembly 22 for puncturing the patient's body and performing the anesthesia procedure.

Figure 4:
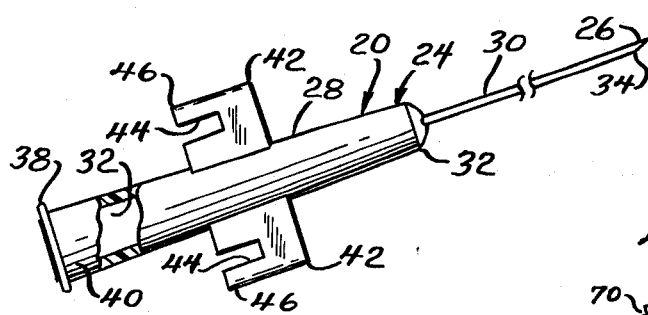
FIG. 4 is a fragmentary elevational view, partly broken away, of the needle means of the device.

Referring to FIG. 4, the needle assembly 24 has a hollow connecting member 28, and a hollow needle 30 extending from a distal end 32 of the connecting member 28 and terminating in the tip 26 adjacent its distal end 34. The connecting member has a cavity 32 extending longitudinally through the connecting member and communicating with the hollow needle 30. As shown in FIGS. 2–4, a tip T of a syringe S may be removably attached to a flange 38 adjacent a proximal end 40 of the connecting member 28 for injecting an anesthetic solution through the connecting member 28 and the hollow needle 30 for performing the anesthesia procedure. As shown in FIG. 4, the connecting member 28 has a pair of connecting tabs or arm means 42 extending outwardly from opposed sides of the connecting member intermediate the proximal and distal ends 40 and 32 of the connecting member. Each of the tabs 42 has a notch extending from a proximal edge of the tabs, and defining an outer hook 46 directed towards the proximal end 40 of the connecting member 28.

Referring to FIGS. 5–8, the sleeve assembly 22 has a hollow abutment member 48 adjacent a proximal end 50 of the sleeve assembly, and a slightly flexible tube 52 extending from a distal end 54 of the abutment member 48. The tube 52 has a proximal end 56 connected to the distal end 54 of the abutment member 48, and a lumen 58 communicating with a cavity 60 extending longitudinally through the abutment member 48. The tube 52 also has an enlarged placement member 62 secured to a distal end 64 of the tube 52.

The abutment member 48 has a proximal end edge 66, and a pair of opposed notches 68 extending slightly from the proximal end edge 66. The connecting member 48 also has a pair of opposed slots 70 and 70' extending from the proximal end edge 66 toward the distal end 54 of the abutment member 48. As shown, the slots 70 and 70' have different lengths, such as ½ inch and ¼ inch, respectively, and the inner ends 72 and 72' of the slots 70 and 70', respectively, terminate at different predetermined distances from the proximal end edge 66 and intermediate the proximal and distal ends 50 and 54 of the abutment member 48. As will be seen below, the notches 68 serve to releasably lock the needle assembly 24 in its first longitudinal position, and the inner ends 72 and 72' of the slots 70 and 70' serve as stops to limit movement of the needle assembly 24 in the sleeve assembly 22 at its second longitudinal positions.

As illustrated in FIGS. 5, 7, and 8, the device 20 also has a guide means 74 slidably attached to the tube 52 of the sleeve assembly 22. The guide means 74 has a ring 76 defining an opening 78 to receive the physician's thumb. The guide means 74 also has an upper flange 80 extending around the tube 52 and defining a longitudinal recess or cutout 82 to snugly receive the tube 52. The flange 80 and upper portion of the ring 76 defining the recess 82 frictionally engage the outer surface of the tube 52, such that the guide means 74 may be slidably moved or adjusted longitudinally along the tube, and is frictionally held in place at a desired location.

Figure 6:
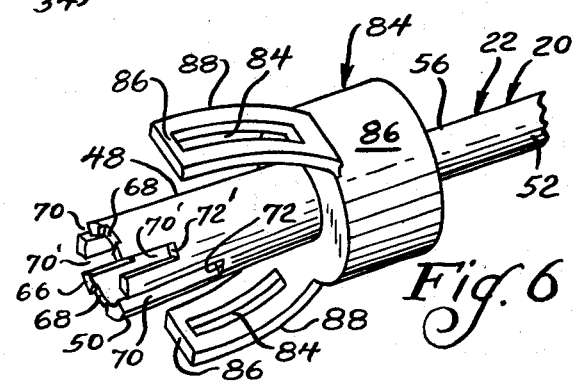
FIG. 6 is a fragmentary perspective view of a proximal end of the sleeve means and a flexible driving member.

As shown in FIGS. 5–7, the device 20 also has a driving member or urging means generally designated 84 which is made of a flexible material, such as rubber. The driving member 84 has an annular retaining member 86 received on the sleeve means adjacent the distal end 54 of the abutment member 48 and adjacent the proximal end 56 of the tube 52, and a pair of flexible straps 88 extending from opposed sides of the retaining member 86 toward the proximal end 50 of the abutment member 48. As best shown in FIG. 7, the abutment member 48 has an enlarged annular flange 90 at the distal end 54 of the abutment member, and the retaining member 86 of the driving member 84 has an annular recess 92 to receive the flange 90 and retain the driving member in place on the device 20. The straps 88 of the driving member 84 have a longitudinal slot 94 defining a rib or connecting portion 96 at the outer ends of the straps 88.

Referring now to FIG. 9, the needle assembly 24 is received within the sleeve assembly 22, with the needle 30 being slidable received within the tube 52. As shown, the tabs 42 of the connecting member 28 in the needle assembly 24 may be received in the notches 68 at the proximal end edge 66 of the abutment member 48 in a first rotational position of the needle assembly relative the sleeve assembly. In this configuration, the needle tip is retracted within the tube 52, and the tabs 42 and notches 68 retain the needle assembly 24 at its first longitudinal position.

As shown in FIG. 10, the ends of the straps 88 may be stretched to position the strap ribs 96 in the notches 44 of the connecting tabs 42, such that the hooks 46 of the tabs extend through the slots 94 of the straps 88. In this configuration, the ends of the straps 88 are retained by the hooks 46, with the straps being in a stretched condition. Accordingly, the flexible straps 88 of the driving member 84 urge the tabs 42 into the notches 68 of the abutment member 48 to releasably lock the needle assembly 24 in its first position.

Referring to FIG. 11, during use of the device, the needle assembly 24 may be slightly withdrawn from the sleeve assembly 22 to withdraw the tabs 42 from the notches 68. Next, the needle assembly 24 is rotated slightly relative the sleeve assembly 22 to position the tabs 42 in alignment with the slots 70 at the proximal end of the abutment member 48 in a second rotational position of the needle assembly. The needle assembly or the syringe attached to the needle assembly may then be released, and the stretched straps 88 of the driving member 84 urge the tabs 42 toward the inner ends 72 of the slots 70, until the tabs 42 engage against the inner ends 72 of the slots at which time forward movement of the needle assembly 24 is stopped. Thus, the needle assembly 24 is driven from its first to second longitudinal position, such that the needle tip 26 extends a predetermined distance from the placement member 62 at the distal end 64 of the sleeve assembly 22 to puncture the patient's body. The inner ends 72 of the slots 70 serve as stop means to prevent overpenetration of the needle tip into the patient's body. Also, the driving member 84 automatically moves the needle assembly 24 from its first to second position without longitudinal force being applied to the needle assembly 24 by the physician.

Alternatively, the needle assembly 24 may be removed from the notches 68, and may be rotated to a third rotational position to position the tabs 42 in the slots 70'. When the needle assembly 24 is released, the driving member 84 urges the tabs 42 toward the inner ends 72' of the slots 70', and forward movement of the needle assembly is stopped at a third longitudinal position with the needle tip 26 again extending from the placement member 62. However, in this configuration the needle tip extends a lesser distance from the sleeve assembly than that previously described in connection with the second rotational position of the needle assembly, since the slots 70' are shorter than the slots 70. Thus, the physician may select a desired distance for penetration of the needle tip by placement of the tabs 42 in the appropriate slots 70 or 70'. In a preferred form, the notches 68 are located intermediate the slots 70 and 70' to facilitate placement of the tabs 42 in either of the slots pairs.

The use of the device is described in connection with FIGS. 1–3, and 9–11. First, the guide means 74 may be slidably adjusted on the tube 52 of the sleeve assembly 22, such that when the physician's thumb is positioned through the opening 78 of the guide means 74, his index and middle fingers extend slightly beyond the placement member 62 at the distal end 64 of the sleeve assembly 22. Next, the straps 88 are positioned with the ribs 96 secured around the hooks 46 of the connecting tabs 42, and the tabs 42 are positioned within the notches 68 at the proximal end of the abutment member 48 to releasably lock the needle assembly 22 in its first longitudinal position with the needle tip 26 retracted within the tube 52. The tip T of the syringe S may be secured to the flange 38 at the proximal end 40 of the connecting member 28 in the needle assembly 24. At this time, the device is ready for use to perform the anesthesia procedure, and, for convenience, it will be described in connection with a paracervical anesthesia procedure.

With the thumb in position in the opening 78 of the guide means 74, and the index and middle fingers extending slightly past the retaining member 62 of the sleeve assembly 22 to retain the distal end of this sleeve assembly during use. The device 20 is then inserted into the birth canal, and the physician determines when the distal end of the sleeve assembly is located at the correct position adjacent the mucosa around the cervical opening for performing the anesthesia procedure.

When the sleeve assembly has been properly placed, the physician may grasp the syringe and retract it slightly to release the tabs 42 from the notches 68 of the abutment member 48, after which the syringe and needle assembly may be turned slightly to align the tabs 42 with the slots 70 or 70' of the abutment member 48. At this time, the physician releases the syringe, and the driving member 84 urges the needle assembly to its second or third longitudinal position, in order that the needle tip penetrates into the mucosa a predetermined distance as defined by the location of the inner ends 72 or 72' of the slots 70 and 70' in the abutment member 48. Next, the physician depresses the plunger P of the syringe S to eject the anesthetic solution through the needle assembly 24 into the mucosa to obtain the paracervical block. The procedure may be performed a plurality of times at the 3 or 4 and 8 or 9 o'clock positions around the cervical opening, after which the device may be withdrawn from the patient's body.

In this manner the anesthesia procedure may be performed through use of the device of the present invention. Since it is unnecessary for the physician to longitudinally force the needle assembly through the sleeve assembly, the possibility that the sleeve assembly may slip out of position before the needle tip penetrates into the mucosa is minimized. Also, since the needle assembly is locked in its first longitudinal position prior to positioning the distal end of the sleeve assembly, the device prevents the needle tip from prematurely projecting from the sleeve assembly and the prematurely puncturing the patient's body. Since it is unnecessary for the physician to longitudinally force the needle assembly through the sleeve assembly, the likelihood that the distal end of the sleeve assembly will be depressed into the mucosa during performance of the anesthesia procedure is minimized, thus preventing overpenetration of the needle tip into the mucosa and minimizing the possibility that the entire assembly may pass through the mucosa, which otherwise may cause harm or possible death to the infant. Additionally, the needle tip is quickly forced into the mucosa by the driving member to reduce trauma to the patient during the anesthesia procedure. However, if desired, the physician may slowly release the syringe to control projection of the needle tip from the sleeve assembly and slow penetration into the mucosa. In this case, it is still unnecessary for the physician to longitudinally force the needle assembly to its second position within the sleeve assembly.

The device also permits the physician to release the driving member from the needle assembly, if desired for a particular purpose. Referring to FIG. 9, the straps 88 may be removed from the tabs 42 of the connecting member 28, and the needle assembly may be locked in its first position, as previously described. As before, the physician rotates the needle assembly within the sleeve assembly, but, in this case, he must longitudinally force the needle assembly through the sleeve assembly.

It will be apparent that the device may be suitably modified within the concepts of the present invention. For example, other devices may be utilized to bias the needle assembly from its first to second position, such as springs, which may push or pull the needle assembly, and which may be located adjacent the proximal or distal ends of the device. Also, it is apparent that the device may be utilized for other suitable procedures, such as a trans-pudendal anesthesia procedure described above.

The foregoing detailed description is given for clearness of understanding only, and no unnecessary limitations should be understood therefrom, as modifications will be obvious to those skilled in the art.

I claim:

1. A device for performing an anesthesia procedure on a patient, comprising: sleeve means having an end portion for placement adjacent the patient's body, hollow needle means received in the sleeve means for relative longitudinal movement thereof, said needle means having a tip for puncturing into the patient's body, and means for biasing the sleeve means and needle means relative each other in a direction exposing said tip from the end portion for puncturing into the patient's body.

2. A device for penetrating into a patient's body, comprising;
elongated sleeve means having a proximal end, and a distal end for placement adjacent the patient's body;
elongated hollow needle means slidably received in the sleeve means and having a tip for puncturing into the patient's body, said needle means being movable between a first longitudinal position with the needle tip retracted in the sleeve means and at least a second longitudinal position with the needle tip extending from the distal end of the sleeve means for puncturing into the patient's body; and means for urging said needle means from its first to second position.

3. The device of claim 2 wherein the urging means is located adjacent the proximal end of the sleeve means.

4. The device of claim 2 wherein the needle means comprises, a hollow needle having a proximal end and a distal end defining said tip, and a connector extending from the proximal end of the needle.

5. The device of claim 4 including syringe means removably attached to said connector.

6. The device of claim 2 wherein said sleeve means is made from a slightly flexible material.

7. The device of claim 2 including guide means attached to said sleeve means to receive the user's thumb.

8. The device of claim 7 including means for slidably attaching said guide means to the sleeve means for longitudinal adjustment to the guide means relative the distal end of the sleeve means.

9. The device of claim 2 including means for releasably locking said needle means in its first position.

10. The device of claim 9 wherein the locking means comprises first abutment means on the needle means and second abutment means on the sleeve means, said first and second abutment means being interengageable to releasably lock the needle means in its first position.

11. The device of claim 9 wherein the locking means comprises, a first abutment member of the sleeve means extending partially around the proximal end of the sleeve means and defining an abutment surface at the proximal end of the sleeve means, and a second abutment member extending outwardly from the needle means, said second abutment member being interchangeable with the abutment surface of the first abutment member to lock the needle means in its first position, said needle means being rotatable in the sleeve means to disengage the first and second abutment members and permit movement of the needle means to its second position.

12. The device of claim 2 including stop means for limiting movement of the needle means at said second position.

13. The device of claim 12 wherein the stop means comprises, a first abutment member on the sleeve means, and a second abutment member extending from the needle means, said abutment members being interengageable at said second position of the needle means to limit movement of the needle means relative the sleeve means at said second position.

14. The device of claim 2 wherein the proximal end of the sleeve means has a proximal end edge and slot means extending from the proximal edge toward the distal end of the sleeve means, and in which said needle means includes arm means extending outwardly from the needle means, whereby said needle means may be positioned at a first rotational position relative the sleeve means to engage the arm means against the proximal edge of the sleeve means and retain the needle means in its first position, and the needle means may be moved to a second rotational position with the arm means aligned with the slot means to permit movement of the needle means to its second position.

15. The device of claim 17 in which the urging means comprises, flexible connecting means extending between said arm means and the sleeve means at a location intermediate said proximal edge and the distal end of the sleeve means, said connecting means being flexed with the needle means located at the first position, whereby the connecting means urges the needle means toward said second longitudinal position.

16. The device of claim 14 wherein the proximal end of the sleeve means includes notch means extending from said proximal edge to receive the arm means with the needle means located at its first rotational position to releasably lock the needle means in its first longitudinal position.

17. The device of claim 2 wherein the urging means comprises, flexible connecting means having a first portion attached to the needle means and a second portion attached to the sleeve means, said connecting means being flexed with the needle means located at its first longitudinal position to urge the needle means toward its second position.

18. The device of claim 17 including means for releasably attaching the connecting means to at least one of said needle means or sleeve means.

19. The device of claim 17 wherein at least one of said needle means or sleeve means includes an outwardly extending connecting tab having a hook directed away from the attachment portion on the other of said needle means or sleeve means, and in which said connecting means includes an opening received on the tab hook.

20. The device of claim 2 in which the sleeve means comprises, a proximal end member, and a resilient tube extending from the proximal end member toward the distal end of the sleeve means.

21. The device of claim 2 including means for selectively applying said urging means to the needle means.

22. The device of claim 2 including means for locking the needle means at a first rotational position of the needle means relative the sleeve means, and means for releasing the needle means at a second rotational position of the needle means relative to sleeve means.

23. The device of claim 2 wherein the needle means is selectively movable between said first longitudinal position and a third longitudinal position with the needle tip extending from the distal end of the sleeve means a lesser distance than in said second longitudinal position, and in which the urging means urges the needle means between said first and third positions.

24. The device of claim 23 including means for stopping the needle means at said third longitudinal position.

25. A device for performing an anesthesia procedure, comprising:
- a sleeve assembly having a hollow abutment member adjacent a proximal end of the sleeve assembly, and a tube extending from the abutment member toward a distal end of the sleeve assembly, said abutment member having a proximal end edge, a pair of opposed slots extending from said proximal end edge a predetermined distance toward a distal end of the abutment member, and a pair of opposed notches located intermediate said slots and extending from said proximal end edge;
- a needle assembly having a connecting member adjacent a proximal end of the needle assembly, and a hollow needle slidably received in said tube and extending from the connecting member to a tip at a distal end of the needle assembly, said connecting member having a pair of opposed connecting tabs extending outwardly from the connecting member, with each of the tabs having a pair of opposed connecting tabs extending outwardly from the connecting member, with each of the tabs having a hood directed toward a proximal end of the tabs, said tabs being received in said notches to releasably lock the needle assembly at a first position with the needle tip retracted within the tube, and said tabs received in said slots for movement of the needle assembly to a second position with the tabs abuttingg against an inner end of the slots and with the needle tip projecting from the distal end of the sleeve assembly; and
- a flexible driving member having a connecting portion secured to the outside of the sleeve assembly intermediate said slots and the distal end of the sleeve assembly, said driving member including a pair of opposed straps having opening means received on said hooks, said straps being stretched with the needle assemble located at its first position, whereby the driving member releasably retains the needle assembly in its first position, and urges the needle assembly from its first to second position when the needle is rotated in the sleeve assembly with the tabs aligned with said slots.

26. A device for performing an anesthesia procedure, comprising: sleeve means having a distal end portion for placement adjacent the patient's body, hollow needle means slidably received in the sleeve means, guide means having opening means to receive the user's thumb, and means for slidably mounting the guide means on the sleeve means to permit longitudinal adjustment of the guide means relative said end portion of the sleeve means.

27. A device for performing an anesthesia procedure, comprising:
- sleeve means having a distal end portion for placement adjacent the patient's body;
- hollow needle means received in the sleeve means for relative longitudinal and rotational movement thereof, said needle means having a tip for puncturing into the patient's body;
- means for releasably locking the needle means at a first rotational position relative the sleeve means with the needle means in a first longitudinal position relative the sleeve means, and with said tip retracted within the sleeve means; and
- means for urging the needle means from said first longitudinal position to a second longitudinal position relative the sleeve means with the tip exposed from the sleeve means for puncturing into the patient's body at a second rotational position of the needle means relative the sleeve means.

28. The device of claim 27 wherein the urging means urges the needle means from said first longitudinal position to a third longitudinal position relative the sleeve means with the tip exposed from the sleeve means a lesser extent that in said second longitudinal position at a third rotational position of the needle means relative the sleeve means.

29. A device for performing an anesthesia procedure, comprising:
- sleeve means having a distal end portion for placement adjacent the patient's body;
- hollow needle means received in the sleeve means for relative longitudinal and rotational movement thereof, said needle means having a tip for puncturing into the patient's body; and
- means for urging the needle means from a first longitudinal position to a plurality of separate longitudinal positions relative the sleeve means at a plurality of associated rotational positions of the needle means relative the sleeve means, with said tip exposed from the sleeve means varying distances in said separate longitudinal positions.

30. A device for performing an anesthesia procedure, comprising:
- sleeve means having a distal end portion for placement adjacent the patient's body;
- hollow needle means received in the sleeve means for relative longitudinal movement thereof, said needle means having a tip for puncturing into the patient's body;
- means for releasably locking the needle means with the tip retracted within the sleeve means;
- means for urging the needle means toward the distal end portion of the sleeve means to expose said tip from the sleeve means when the locking means is released; and
- means for selecting the distance said exposed tip extends from the sleeve means.

* * * * *

UNITED STATES PATENT AND TRADEMARK OFFICE
CERTIFICATE OF CORRECTION

PATENT NO. : 3,995,629
DATED : December 7, 1976
INVENTOR(S) : Bhupendra C. Patel It is certified that error appears in the above-identified patent and that said Letters Patent are hereby corrected as shown below:

Column 1, line 43, "in" should be -- In -- .

Column 1, line 59, after "assembly" insert -- while the assembly -- .

Column 2, line 9, "teh" should be -- the -- .

Column 3, line 51, "towards" should be -- toward -- .

Column 5, line 39, "slots" should be -- slot -- .

Column 8, line 24, "17" should be -- 14 -- .

Column 9, line 36, "abuttingg" should be -- abutting -- .

Column 9, line 45, "assemble" should be -- assembly

Signed and Sealed this

Fifteenth Day of February 1977

[SEAL]

Attest:

RUTH C. MASON
*Attesting Officer*

C. MARSHALL DANN
*Commissioner of Patents and Trademarks*